(12) United States Patent
Spriggs

(10) Patent No.: US 9,897,525 B2
(45) Date of Patent: Feb. 20, 2018

(54) RELATING TO PARTICLE CHARACTERISATION

(71) Applicant: Malvern Instruments Limited, Malvern, Worcestershire (GB)

(72) Inventor: David Spriggs, Malvern (GB)

(73) Assignee: Malvern Instruments Ltd., Malvern (GB)

( * ) Notice: Subject to any disclaimer, the term of this patent is extended or adjusted under 35 U.S.C. 154(b) by 18 days.

(21) Appl. No.: 15/139,128

(22) Filed: Apr. 26, 2016

(65) Prior Publication Data

US 2016/0320284 A1    Nov. 3, 2016

(30) Foreign Application Priority Data

May 1, 2015    (EP) .................................. 15166133

(51) Int. Cl.
*G01N 15/02*    (2006.01)
*G01N 21/47*    (2006.01)
(Continued)

(52) U.S. Cl.
CPC ..... *G01N 15/0211* (2013.01); *G01N 15/0227* (2013.01); *G01N 15/1434* (2013.01);
(Continued)

(58) Field of Classification Search
CPC ............................... G01N 15/02; G01N 21/00
USPC .................................................. 356/335–343
See application file for complete search history.

(56) References Cited

U.S. PATENT DOCUMENTS 5,824,269 A * 10/1998 Kosaka .............. G01N 15/1459
250/461.2
5,880,835 A * 3/1999 Yamazaki ............ G01N 15/147
356/336
(Continued)

FOREIGN PATENT DOCUMENTS

EP        0 559 529        9/1993
JP       2000-146817       5/2000
(Continued)

OTHER PUBLICATIONS

Shapiro,(2003) "How Flow Cytometers Work", Practical Flow Cytometry, 4th Edition, John Wiley & Sons, Inc., ISBN: 0-471-41125-6, 123 pages.

(Continued)

*Primary Examiner* — Roy M Punnoose
(74) *Attorney, Agent, or Firm* — Morrison & Foerster LLP

(57) ABSTRACT

A particle characterization apparatus is disclosed comprising: a first light source; a second light source, a sample cell; a first detector and a second detector. The first light source is operable to illuminate a first region of a sample comprising dispersed particles within the sample cell with a first light beam along a first light beam axis so as to produce scattered light by interactions of the first light beam with the sample. The first detector is configured to detect the scattered light. The second light source is operable to illuminate a second region of the sample with a second light beam along a second light beam axis. The second detector is an imaging detector, configured to image the particles along an imaging axis using the second light beam. The first light beam axis is at an angle of at least 5 degrees to the second light beam axis.

14 Claims, 4 Drawing Sheets

(51) Int. Cl.
*G01N 21/53* (2006.01)
*G01N 15/14* (2006.01)
*G01N 15/06* (2006.01)

(52) U.S. Cl.
CPC ........... *G01N 21/47* (2013.01); *G01N 21/532* (2013.01); *G01N 15/1436* (2013.01); *G01N 2015/0693* (2013.01); *G01N 2015/1493* (2013.01)

(56) References Cited

U.S. PATENT DOCUMENTS

| | | | | |
|---|---|---|---|---|
| 6,061,130 | A * | 5/2000 | Plate | G01N 15/0227 356/335 |
| 6,177,994 | B1 * | 1/2001 | Watson | G01N 15/0211 356/337 |
| 7,379,577 | B2 * | 5/2008 | King | G01N 15/0227 356/335 |
| 7,471,393 | B2 | 12/2008 | Trainer | |
| 8,842,267 | B2 | 9/2014 | Heine et al. | |
| 2005/0105077 | A1 | 5/2005 | Padmanabhan et al. | |
| 2007/0146873 | A1 | 6/2007 | Ortyn et al. | |
| 2016/0252443 | A1 * | 9/2016 | Spriggs | G01N 15/1456 356/336 |

FOREIGN PATENT DOCUMENTS

| | | |
|---|---|---|
| WO | WO 2013/027034 | 2/2013 |
| WO | WO 2013/173446 | 11/2013 |

OTHER PUBLICATIONS

Extended European Search Report, dated Oct. 21, 2015 directed towards European Patent Application No. 15166133.7, 9 pages.

* cited by examiner

RELATING TO PARTICLE CHARACTERISATION

CROSS REFERENCE TO RELATED APPLICATION

This application is a U.S. Non-Provisional patent application claiming priority to European Patent Application No. EP15166133, filed May 1, 2015, and is hereby incorporated by reference in its entirety.

FIELD OF THE INVENTION

The present invention relates to an apparatus for characterising particles, and to a method for use in characterising particles. Characterising particles may comprise determining a distribution of particle size.

BACKGROUND

It is known that particles in a sample can be characterised by illuminating the sample and measuring the light scattered by the particles. The particles of the sample are typically dispersed within a sample cell in a dispersant medium during measuring. The dispersant medium is typically air or water, and typically flows through the sample cell during measurement.

The correlation between light scattering and particle characteristics can be described by the well-known Mie solution to Maxwell's equations. Smaller particles tend to result in larger scattering angles, and larger particles result in smaller scattering angles. The light scattered at each of a range of angles from the sample can be used to determine, for example, a size distribution of the particles in the sample. Such a measurement may be referred to as a light (e.g. laser) diffraction particle characterisation.

Much of the development of instruments for light diffraction particle characterisation has been directed towards increasing the size range of particles that can be characterised at one time. At the same time, there is a demand to reduce the size of the instrument. The requirements for a greater measurement range and a smaller instrument are in conflict, which may result in technical difficulties in achieving sufficient performance, or a reduced quality of measurement. In particular, the technical requirements for achieving accurate characterisation of larger particles are particularly challenging and expensive. There may be a discrepancy between the cost of the components needed to achieve large particle characterisation and the perceived value associated with these measurements.

An instrument for characterisation of particles by light diffraction typically works by measuring the intensity of light scattered by fine particles suspended in a strong monochromatic light source of known intensity. The instrument needs to measure the intensity of light at a series of angles measured from the illumination direction, because different sizes of particles scatter light at different angles. Generally a large particle will scatter light at an angle very close to the axis of the illuminating beam, and a smaller particle will scatter light at a larger angle. Because the illuminating beam is much stronger than the scattered light a detector is typically used that allows light to pass through without touching the detector. Otherwise, the illumination beam incident on the detector would produce a very large reflection that can leak into neighbouring detectors. The reflected light would tend to bounce all around the inside of the instrument, overwhelming the much smaller scattered light signals.

Larger particles scatter light at angles close to the axis of the illumination beam (e.g. a laser). To separate the scattered light from the illumination light it is necessary either to measure with detectors close to the focused spot of the illumination beam, or to use a longer focal length in order to allow the illumination beam and scattered light to separate out. The former approach means that the detector and illumination beam must be very accurately aligned, and the second approach results in a very long instrument that may have stability problems.

As particle size becomes smaller, the useful scattered light changes in two ways. The peak intensity is scattered at a larger angle to the illumination beam axis and the scattering becomes more isotropic. A size of particle will eventually be reached where the scattered light is almost completely isotropic, and therefore the instrument cannot tell the difference between particles at this size and particles that are smaller. This sets the lower size limit for a light diffraction instrument. However, because the particle size at which the scattering becomes isotropic depends on the wavelength of the light, it is possible to extend the bottom size limit for an instrument by changing to a shorter wavelength light source.

One approach is to use a red Helium Neon laser at 633 nm to measure the largest particles and a blue non-coherent light source (such as an LED or filtered incandescent lamp) to allow measurement of the fine particles. A large component of the cost of such an instrument is associated with the components needed to measure the large particles: the laser must have a very high beam quality, and the detector must be positioned to almost sub-micron tolerances.

One solution might be to limit the maximum particle size that may be characterised by the instrument, but even when measuring fine particles it is often desirable to be confident that there are no large particles present. Any system that limits the top size too far may also limit the ability to report problems with aggregates and contaminants.

A solution that addresses or ameliorates at least some of the above mentioned problems is desired.

BRIEF SUMMARY OF THE INVENTION

According to the present invention, there is provided a particle characterisation apparatus comprising: a first light source; a second light source, a sample cell; a first detector and a second detector; wherein:

the first light source is operable to illuminate a first region of a sample comprising dispersed particles within the sample cell with a first light beam along a first light beam axis so as to produce scattered light by interactions of the first light beam with the sample;

the first detector is configured to detect the scattered light;

the second light source is operable to illuminate a second region of the sample with a second light beam along a second light beam axis;

the second detector is an imaging detector, configured to image the particles along an imaging axis using the second light beam; and the first light beam axis is at an angle of at least 5 degrees to the second light beam axis.

The first light beam axis may be at an angle of at least: 10, 15, 20, 25 or 30 degrees to the second light beam axis.

The imaging axis may be at an angle of at least: 5, 10, 15, 20, 25, or 30 degrees from the first light beam axis.

The sample cell may comprise a first wall and a second wall. The first light beam may pass through the first wall, then through the sample, then through the second wall. The first and second wall of the sample cell may each comprise a convex external surface through which the first light beam axis and the second light beam axis passes.

The first and second wall may each comprise a plano-convex lens defined by the respective convex external surface, the optical axes of the first and second wall defining a sample cell optical axis.

The second light beam axis may be at an angle of at least 10° to the sample cell optical axis.

The first light source, sample cell and first detector may define a scattering plane, and the second light source and second detector may be disposed offset from the scattering plane, occupying a different azimuthal orientation about the first light beam axis.

The first light source may be coherent. The second light source may be incoherent.

The second detector may comprise a two dimensional array of light sensitive elements.

The first detector may comprise an array of detector elements, arranged to detect light scattered at a range of scattering angles.

The first light source may have a wavelength of less than 550 nm. The first light source may have a wavelength of less than 500 nm, 450 nm or 400 nm.

The particle characterisation apparatus may comprise an imaging lens between the second detector and the sample cell. The imaging lens may comprise an entocentric lens.

The particle characterisation apparatus may further comprise a collecting lens between the sample cell and the first detector. The collecting lens may comprise an aspheric surface.

The collecting lens may comprise an optical axis that is coincident with the first light beam axis.

The processor may be configured to correct a size of an imaged particle based on a location of the particle image at the second detector.

The particle characterisation apparatus may further comprise a condenser lens between the second light source and the sample cell. A collector lens may be provided between the condenser lens and the second light source. The second light source, collector lens and condenser lens may be arranged to provide Köhler illumination of a region within the sample cell.

The second detector may be arranged on a path of the second light beam, so as to perform light field imaging of particles within the sample cell.

The second detector may be arranged off the path of the second light beam, so as to perform dark field imaging of particles within the sample cell.

The particle characterisation apparatus may comprise a third light source arranged to provide a third light beam that is not directly received by the second detector, so that the apparatus is configured to perform dark field imaging when the sample is illuminated by the third light source and not by the second light source.

The particle characterisation apparatus may further comprise a light trap behind a sample cell region that is imaged by the second detector.

The light trap may be provided around the second light source, for providing a dark field background when the sample is illuminated by the third light source.

The apparatus may be configured to perform a static light scattering measurement to derive a particle size from an output of the first detector. The apparatus may be configured to perform a dynamic light scattering measurement from an output of the first detector.

The first region may be at least partly coincident with the second region.

The apparatus may comprise a processor, configured to correlate or cross-reference data from the first detector with data from the second detector (or vice-versa). The output from the second detector may be used to improve a measurement derived from the first detector (and vice versa). This may be particularly applicable where the first (scattering detection) region is at least partly co-incident with the second (imaging detection) region.

The output from the second detector may be used to identify or confirm particle aggregation or breakup, check the uniformity of mixing, and gate data from the first sensor when the sample appears atypical. The second detector may identify particles that are too large to be measured by the first detector. While such particles are within the first illumination beam, the output of the first detector may be ignored or discarded. This may improve the fidelity of a measurement.

Where the second detector identifies that particles of a specific size range are present in the sample, a mathematical model used to relate the scattered light measured at the first detector to a particle size distribution may be constrained to include particles of this size range. This may improve the speed and reliability with which measurements from the first detector can be related to particle characteristics.

Embodiments of the invention will now be described, purely by way of example, with reference to the accompanying drawings, in which:

BRIEF DESCRIPTION OF THE DRAWINGS

The invention is described in further detail below by way of examples and with reference to the accompanying drawings, in which.

DETAILED DESCRIPTION

Figure 1:
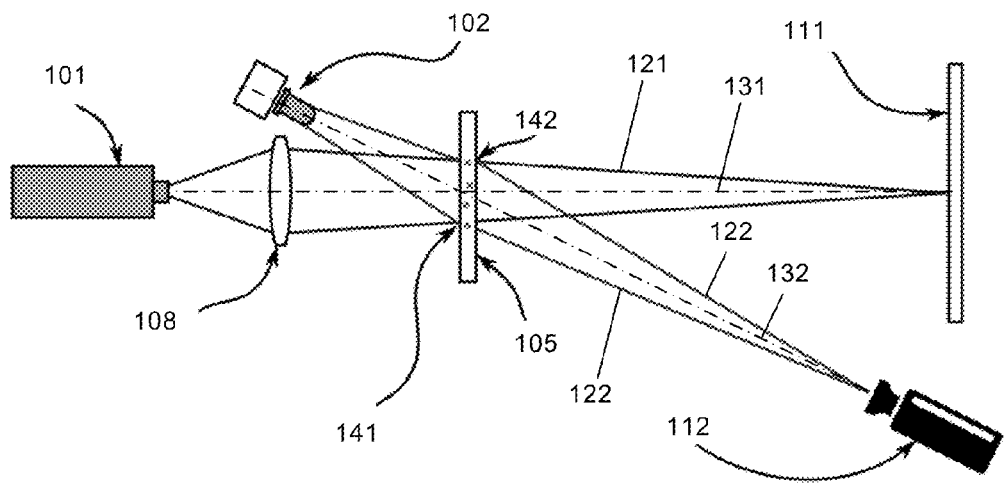
FIG. 1 is a schematic diagram of an instrument in which an imaging detector with light field illumination is combined with a scattering detector.

A number of arrangements are possible for a hybrid instrument that both images particles and detects scattered light from particles.

One approach is to use the light source for light scattering (which is usually a laser) as a light source. The imaging detector can be placed on the opposite side of the sample cell to the light source, which results in a bright field illumination, with the particles appearing as dark shapes against a bright background. This approach has a number of disadvantages. A laser light source typically has a Gaussian intensity profile, which means that particles at the edge of the light beam are less brightly illuminated than particles in the centre of the light beam. Furthermore, because of the coherency of the light, the edges of dark particles will be blurred by diffraction rings. In addition, the laser cannot be allowed to clip edges of the sample cell, or stray light will be scattered as diffraction lines. This means that there must be a dark area at either side of the sample cell with no illumination, which means that some particles cannot be imaged.

Another approach is to use a different light source for imaging illumination, with beam splitters and dichroic mirrors to allow the imaging illumination and imaging detector to image through the light scattering illumination axis. A quarter wave plate (and perhaps a polariser) may be needed to eliminate back-reflection from the imaging detector focal plane array, which may interfere with any back-scattering measurements. If the dichroic mirrors are left in place, stray reflections may be caused that could distort the backscatter measurements.

A further approach is to use an first and second sample cell connected in series, and perform light scattering measurements on the sample as it passes through the first cell, and particle imaging as the sample passes through the second cell. A drawback with this approach is that there is a time lag between the scattering and imaging measurements on the same portion of a flowing sample, making it difficult to successfully correlate the different types of measurement. Combined measurements of time dependent particle phenomena, such as crystallisation and aggregation, are not possible with such an arrangement.

Furthermore, the use of a first and second sample cell in a flow circuit will increase pressure drop along a fluid circuit comprising the first and second sample cell. Increased pump pressure would therefore be needed. The increased pump power and pressure associated with such an arrangement is more likely to alter fragile particles and emulsions. In addition, adding a further sample cell adds a great deal of extra cost. The cost of an imaging sample cell would be similar to the cost of a scattering sample cell, as it would be performing a similar function.

A separate second flow cell (for imaging) also may make a fluid path comprising the first and second flow cell more difficult to fill, drain and clean. If the second (imaging) flow cell were placed at the same height as the first (scattering) cell, then there would be areas in the piping between the two cells that would form u-bend sumps, and would not drain properly. In addition there would be upper loops of piping that may form air traps. Bubbles could be shed at any time to contaminate measurements, and the fluid path would be restricted. If the imaging sample cell were placed at a different height (e.g. above or below the scattering sample cell), the combined instrument would be much taller. Although such a system might drain adequately, it would be difficult to fill, due to the increased pump head needed to prime the system and clear air out of the pipes.

Referring to FIG. 1, an instrument is shown, comprising first light source 101, second light source 102, sample cell 105, first detector 111, second detector 112 and illumination lens 108.

The sample cell 105 comprises a sample 150, held between a first and second cell wall 141, 142. In this example the interior and exterior surfaces of each cell wall are flat and parallel, but in other embodiments this may not be so. The sample 150 comprises particles dispersed in a fluid, such as water.

The first light source 101, illumination lens 108 and first detector 111 are configured to perform a static light scattering measurement. The first light source 101 is configured to illuminate a first region of the sample 150 within the sample cell 105 by producing a first light beam 121 along a first light beam axis 131. The first light beam 121 and first light beam axis 131 pass through the illumination lens 108, then through the first wall 141 of the sample cell 105, through the sample 150 and through the second wall 142 of the sample cell 105. The first light beam 121 may be focussed near the first detector 111, but preferably does not illuminate the first detector 111. The first detector 111 may, for instance, include a hole through which the first light beam 121 passes. The first light beam 121 may be received in a light trap (not shown). The light trap may include light measuring means (not shown) for measuring the power of the first light beam 121.

The first light source 101 may comprise a coherent light source, for example having a wavelength of less than 550 nm. For example the first light source 101 may comprise a blue or violet laser. The first light source 101 may comprise a laser diode.

The illumination lens 108 produces a first light beam 121 that illuminates the first region of the sample. The first light beam 121 may converge through the sample, be collimated in the sample, or may diverge in the sample.

The first detector 111 is configured to detect light scattered by interactions of the first light beam 121 with the particles of the sample 150 in the first region (which may be referred to as a scattering region). The first detector 111 may comprise a plurality (e.g. an array) of detector elements each corresponding with a different range of scattering angles. The detector elements may each comprise photodiodes (for example, formed on a silicon substrate). The first detector 111 may for instance, comprise a one dimensional array of detector elements. Each detector element may be annular, with the centre of each annulus substantially coincident with the first light beam axis 131. Alternatively, each detector element may be arc shaped, with the centre of each arc co-incident with the first light beam axis 131.

In this example, the first detector 111 is arranged to detect forward scattered light. Forward-scattered light may be defined as light that is scattered in a direction that is at less than or equal to 90 degrees from the direction of the first light beam axis 131, with back-scattered light being defined as light that is scattered in a direction that is more than 90 degrees from the direction of the first light beam axis 131.

The second light source 102 produces a second light beam 122 along a second light beam axis 132. The second light beam 122 illuminates a second region of the sample cell 105 that overlaps with the first region. The second region may comprise (or contain) the first region. The second light source 102 is preferably configured to provide substantially uniform illumination of the second region. The second region may encompass the breadth of the sample cell 105 (lateral to a flow direction through the sample cell 105).

The second light source 102 may comprise a non-coherent light source, such as an LED, incandescent lamp, or any other light source. The second light source 102 may be broad band (i.e. comprising more than one wavelength of light), or may be monochromatic.

The second detector 112 is an imaging detector (such as a camera), and is configured to image particles within the second region along an imaging axis. The imaging axis in this embodiment is coincident with the second light beam axis 132. The second detector 112 may be arranged to image a third region of the sample 150 (which may be referred to as an imaging region), so that measurements from the first detector 111 and second detector 112 may be compared and correlated (for example, as a function of time). The imaging region may be arranged to be substantially coincident with, or a subset of, the scattering region. An imaging lens (not shown) may be provided for focussing light from the imaging region onto a focal plane of the second detector 112.

For example, the output from the first detector 111 may be used to determine a first particle size distribution. For example, the first detector 111 may be arranged to detect diffracted light from the particles, and the instrument may be configured to perform a light diffraction measurement (e.g. static light scattering) by processing the output of the first detector to determine a first particle size distribution based on Mie theory (or the Fraunhofer approximation).

The instrument may be configured to determine a second particle size distribution, using the output from the second detector. The second particle size distribution may be determined by processing images of particles. A first range of particle size that may be characterised using data from the second detector will be constrained by at least one of the diffraction limit of the optics, the wavelength of the second light source and the spatial resolution of the second detector. As already discussed, a second range of particle sizes that can characterised by a light diffraction measurement is also constrained (at the upper limit by path length and minimum scattering detection angle). The instrument may be configured such that the first range of particle size partially overlaps with the second range of particle size.

Parameters for adjusting the first particle size distribution may be determined from comparing the second particle size distribution with the first particle size distribution. For example, the first particle size distribution may be adjusted to match the second particle size distribution in the region of overlap between the first and second range of particle size.

In some embodiments the instrument may also be configured to determine particle shape parameters using the data from the second detector. The particle shape parameters may be used to adjust the first particle size distribution. For example, Mie scattering theory is based on the assumption that particles are spherical. Where the particle shape parameters indicate that the particles are not generally spherical, a correction may be applied to the first particle size distribution to account for this. The correction may be selected to make the first particle size distribution match the second particle size distribution in the region of overlap.

In some embodiments, the second particle size distribution may be used to calibrate the first particle size distribution in the region of overlap. The first particle size distribution may alternatively be used to calibrate the second particle size distribution in the region of overlap.

The first and second particle size distributions may be combined together to form a single common distribution over the combined first and second range of particle size.

The first light source 101 and second light source 102 may be configured to be rapidly switched on and off, to alternate illumination of the sample 150 by the first and second light beam 121, 122 respectively. The period of switching may be less than: 10 seconds, 5 seconds, 1 second, 500 ms, 250 ms, 100 ms, or 50 ms. Such an approach eliminates any stray light contamination of a scattering measurement with the second light beam, and of the imaging measurement by the first light beam. Alternatively, the first light source 101 and second light source 102 may be configured to illuminate the sample 150 at the same time, to allow simultaneous measurement by scattering and imaging.

An instrument in which the first light beam axis 131 is at an angle to the second light beam axis 132 can be arranged so that none of the imaging components lie on scattering planes, defined by the sample cell and the elements of the first detector 111. This greatly reduces the chance of stray reflections distorting scattering measurements. Backscatter measurements (for very small particles) may therefore be without contamination from the second light source. In addition, following this approach an instrument may be produced that does not include at least one of: beam splitters, mirrors, polarisers, quarter wave plates or other moving elements for switching between modes (scattering and imaging). An instrument can thereby be produced that is both low cost and reliable.

In some embodiments, a requirement for the scattering measurement arrangement (comprising the first light source 101 and first detector 111) to characterise larger particles (for instance, larger than 100 μm) may be relaxed, and the imaging measurement arrangement (comprising the second light source 102 and second detector 112) may be relied on to characterise these larger particles. In such an arrangement, the scattering measurement arrangement may be made relatively low cost, by using a single, short wavelength light source (for example below 550 nm), such as a blue or violet laser diode.

An instrument with a single wavelength first light source 101 (for the scattering measurement arrangement) can use a more simple anti-reflective (AR) coating on optical elements associated with the scattering measurement arrangement. Such single wavelength AR coatings have reduced cost and are simpler to produce.

Since the sample cell 105 is relatively thin, an entocentric lens may be used to image particles on the second detector (rather than a telecentric lens).

The inclination of the imaging axis relative to the sample cell 105 means that the distance from the focal plane of the second detector 112 is not uniform across the imaging region of the sample 150. Particles at the top of the sample cell 105 (as shown in FIG. 1) will be further away from the second detector 112 than particles at the bottom of the sample cell 105. This may cause the particles in different positions within the imaging region to have different magnification at the focal plane. The instrument may be configured to compensate for such magnification (e.g. using a processor), based on the position of the imaged particle on the second detector 112.

Figure 2:
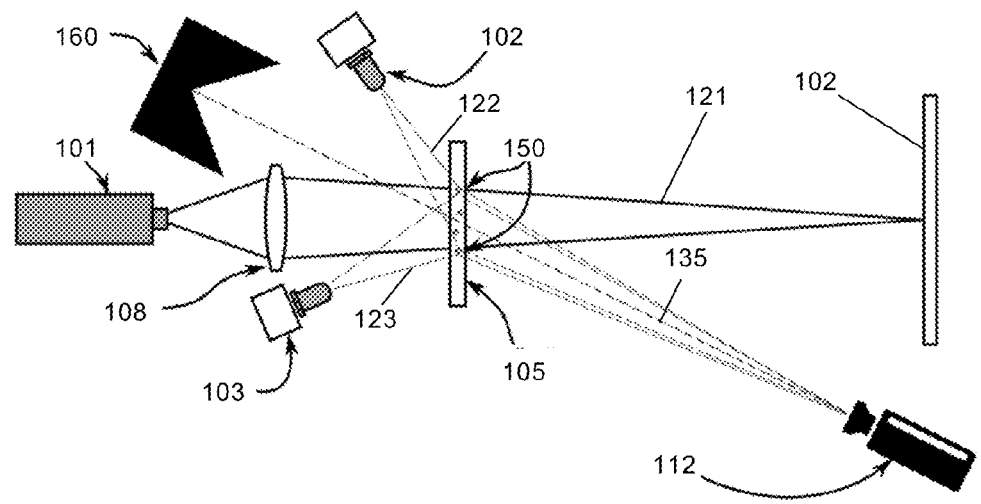
FIG. 2 is a schematic diagram of an instrument in which a scattering (first) detector is combined with an imaging (second) detector, with dark field illumination.

Referring to FIG. 2, an alternative instrument is shown, comprising first light source 101, second light source 102, third light source 103, sample cell 105, first detector 111, second detector 112, illumination lens 108 and light trap 160.

In this arrangement the scattering measurement arrangement may include any of the features described with reference to FIG. 1.

The second light source 102 in this instrument also produces a second light beam 122 along a second light beam axis 132. The second light beam 122 illuminates a second region of the sample cell 105 that overlaps with the first region (illuminated by the first light beam 121, as described with reference to FIG. 1). The second region may comprise (or contain) the first region. The second light source 102 is preferably configured to provide substantially uniform illumination of the second region. The second region may encompass the breadth of the sample cell 105 (lateral to a flow direction through the sample cell 105).

Although these features are in common with the arrangement of FIG. 1, in the arrangement of FIG. 2 the second light beam axis is not coincident with (or parallel to) the imaging axis 135. Instead there is an angle between the second light beam axis and the imaging axis 135, which may be at least 15 degrees. The angle between the second light beam axis and the imaging axis 135 is selected such that the second detector 112 does not receive light directly from the second light source 102. Instead, the second detector 112 is arranged to receive only light from the second light beam 122 that has interacted with particles of the sample, for instance by reflection or refraction. Such reflection will result in a highlight line at the edge of each particle, imaged on a dark field (i.e. a dark background image).

Dark field imaging may be more appropriate for particles that are translucent or completely transparent, which may be less visible in a light field imaging arrangement.

A third light source 103 may be provided, producing a third light beam 123 along a third light beam axis. The third light beam 123 illuminates at least part of the second region of the sample cell 105. The third light beam axis is at a different (non-zero) angle to the imaging axis 135. The angle between the third light beam axis and the imaging axis 135 is selected such that the second detector 112 does not receive light directly from the third light source 103. The third light source 103 is arranged to highlight edges of particles from a different direction.

The light trap 160 may be arranged to improve the contrast between the bright particle images and the dark field background, by trapping stray light behind the sample cell 105 along the imaging axis 135. The light trap 160 is thereby configured to provide a dark(er) background to the imaged particles.

Further dark field light sources may be provided (not shown), similar to the second and third light source 102, 103, to provide further dark field illumination of the sample 150 from behind the sample cell 105 (relative to the second detector 112). If sufficient light sources arranged in this way are provided, the highlight lines around the edge of each particle will form a continuous bright perimeter around each particle within the imaging region.

The light beam axis of each dark field light source may be at an angle of less than 60 degrees (or less than 45 degrees) to the imaging axis 135. Keeping this angle relatively low means that the reflections from the particles received by the second detector are at a relatively low reflection angle. This in turn means that specular reflections from the particle surfaces are enhanced, increasing the contrast of the imaged particles.

As for the light field arrangement of FIG. 1, the dark field light sources 102, 103 may be switched off during a light scattering arrangement, or simultaneous measurement by scattering and imaging may be used.

Figure 3:
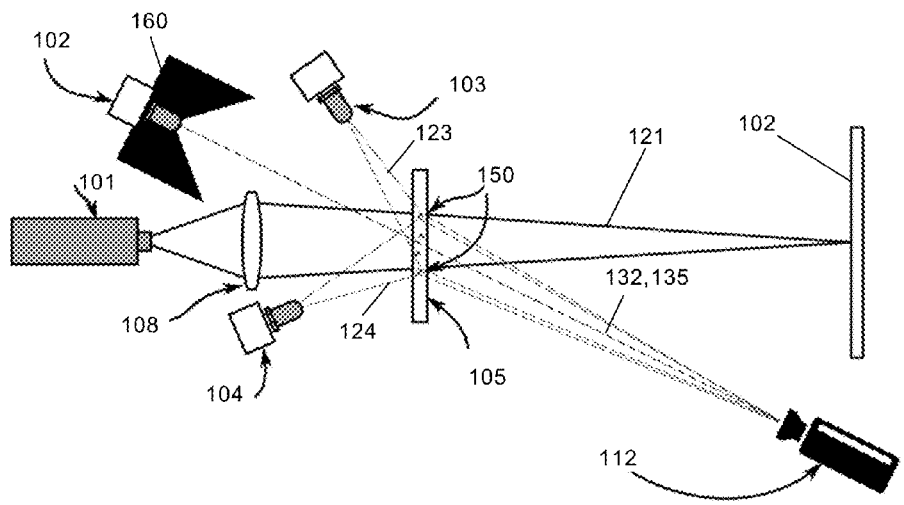
FIG. 3 is a schematic diagram of an instrument in which an imaging detector with both dark field and light field illumination is combined with a scattering detector.

In some instruments, both light field and dark field illumination may be provided, by combining light field and dark field light sources. FIG. 3 shows an example of such an instrument, comprising a first light source 101, second light source 102, third light source 103 and fourth light source 104. A first detector 111 for detecting scattered light and second detector 112 for imaging are provided, configured in the same way as in the examples of FIGS. 1 and 2. A light trap 160 may be provided behind the sample cell 105 (from the point of view of the second detector 112), along the imaging axis 135.

The first light source 101 is configured in the same way as the first light source of FIGS. 1 and 2, to provide a first light beam 121 for performing scattering measurements. The second light source 102 is configured to provide light field illumination for the second detector 112, in the same way is the example of FIG. 1, but in this embodiment the second light source 102 may be surrounded by a light trap 160. Third and fourth light sources 103, 104 are arranged to provide dark field illumination of the sample 150 for imaging by the second detector 112, in the same way as explained with reference to FIG. 2.

In this arrangement, either dark field light sources 103, 104, or bright field light source 102 can be used to illuminate the sample 105 for imaging by the second detector 112.

An instrument may be configured to capture sequential bright field and light field images that are close together in time (for instance with less than 1 s, 0.5 s. 250 ms or 100 s) of separation. The bright field and light field image may be correlated or otherwise combined together to improve the characterisation of particles by imaging. For example, the bright field image could be inverted and summed with the dark field image. Any particle edges that were missing or of low contrast in one image could be supplied by the other image. The maximum tolerable time delay between bright field and dark field imaging may be determined based on a flow rate of the sample 150. If the sample 150 is flowing at a high rate, particles will move a significant distance in a relative short time, which may make combining the images more complex.

Figure 4:
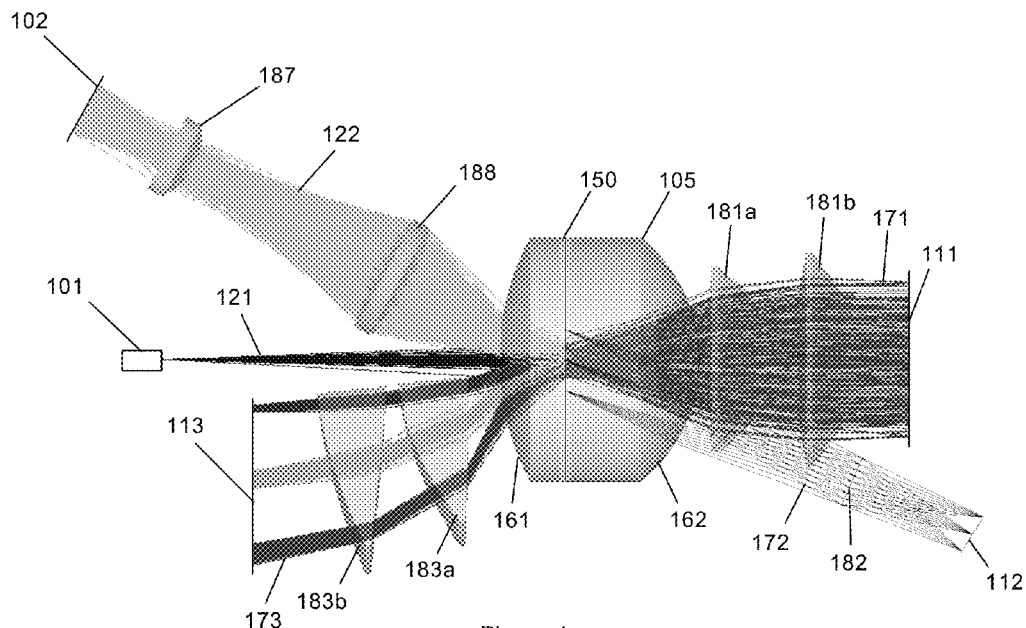
FIG. 4 is a ray diagram of an instrument with a back-scattered light detector, a forward-scattered light detector, and imaging detector with light field illumination.

FIG. 4 shows a further instrument, comprising a first light source 101, second light source 102 and sample cell 105. The first light source 101 may be a coherent light source, such as a laser. The second light source may be incoherent, such as an LED. The first light source 101 is configured to illuminate a sample 150 within the sample cell 105 using a first light beam 121 along a first light beam axis, so as to produce scattered light 171, 173 by interaction of the first light beam 121 with particles of the sample 150. The scattered light comprises forward scattered light 171 and backward scattered light 173. The first light beam 121 passes through a first wall of the sample cell 105, then through the sample 150 and then through the second wall of the sample cell 105.

The instrument further comprises a first detector 111 and third detector 113, configured to detect the scattered light 171, 173. The first detector 111 is arranged to detect forward scattered light 171, and the third detector 113 is arranged to detect backward scattered light 173. First collection lenses 181a, 181b are provided to collect and focus forward scattered light 171 at the first detector 111, and second collection lenses 183a, 183b are provided to collect and focus backward scattered light 173 at the third detector 113. The first detector 111 and third detector 113 are each positioned in different azimuthal locations (with respect to the first light beam axis). In this example the first detector 111 and third detector 113 are at an azimuthal offset of 90°, so that if the first detector 111 receives S polarised scattered light, the second detector receives P polarised scattered light. This may substantially reduce the amount of optical noise at each of the first and third detector 111, 113 by positioning one of these detector away from reflections from the other detector.

Each of the collection lenses 181a, 181b, 183a, 183b may comprise an aspheric surface. Each of the collection lenses 181a, 181b, 183a, 183b are sector shaped, when viewed along the first light beam axis, are positioned with their optical axes coincident with the first light beam axis, and comprise an open region to allow the first light beam 121 to pass by them without contributing to stray light by reflecting from the lenses 181a-b, 183a-b. This open region of each collecting lens substantially reduces optical noise, and means that reduced surface quality (contributing to light scattering) that may be associated with aspheric surfaces is less of an issue, since the first light beam 121 does not pass through the aspheric surface. The ability to use aspheric surfaces contributes significantly towards achieving a compact, high-performance scattered light detection arrangement.

The first wall of the sample cell 105 may comprise a convex external surface 161 through which the first light beam 121 passes, and the second exterior wall of the sample cell 105 may comprise a convex external surface 162 through which the first light beam 121 passes. Each of the first and second wall may comprise a plano-convex lens, each comprising a flat internal sample cell surface.

An effect of the curved external surfaces 161, 162 of the sample cell walls is to allow light scattered at higher angles to escape with less refraction at the sample cell air interface. Flat external surfaces result in spreading out of scattered light as it is refracted at the sample cell wall/air interface, and a critical angle exists at which scattered light is totally internally reflected. The use of a sample cell 105 with a convex external surface 161 or 162 enables both a broader range of scattering angles to be detected, increases the amount of scattered light per steradian outside the sample cell (because scattered light is not spread by refraction at the sample cell/ait interface) and reduces optical noise (because any totally internally reflected scattered light ends up as optical noise). Furthermore, the convex external walls 161, 162 decrease deleterious effects of detecting light from the sample cell 105 at high angles (relative to a normal to the plane defined by the interior surfaces of the sample cell 105), as well as increasing the range of angles over which light from the sample 150 may be detected. This makes it more straightforward to arrange multiple detection modalities around the sample cell 105 with different detection/imaging axes and different illumination axes (such as scattering detectors 111, 113 and imaging detector 112).

Each of the first detector 111 and third detector 111, 113 may comprise an array of light sensitive elements, each element for detecting light scattered at a different range of angles. The first detector 111 may be configured to detect light scattered at angles of around 20° to around 70°. The range of scattering angles detected at the first detector 111 may include scattering angles that are higher than the critical angle for a flat walled cell. The range of scattering angles detected by the first detector 111 may be at least 30° (e.g. from 20° to 50°). A further detector (not shown) may be configured to detect lower scattering angles. The scattered light detected by the further detector may be focussed on the further detector by the second sample cell wall.

The second detector 112 comprises an imaging detector. The plane of an imaging lens 182 is schematically illustrated in FIG. 4, showing how the sample 150 may be imaged at the second detector 112. The second light source 102 is configured to provide bright field illumination of the sample 150, and is configured to produce a second light beam 122 along a second light beam axis. The second light beam axis is substantially coincident with the imaging axis of the second detector 112, and the second light source 112 thereby provides bright field illumination of the sample 150.

In order to provide a high uniformity of illumination, at least one lens may be provided between the second light source 102 and the sample cell 150. In FIG. 4 a collector lens 187 and condenser lens 188 are provided between the second light source 102 and the sample cell 105, so as to provide for a Köhler type optical arrangement in which substantially uniform illumination of the first region of the sample cell 105 is provided.

Figure 5:
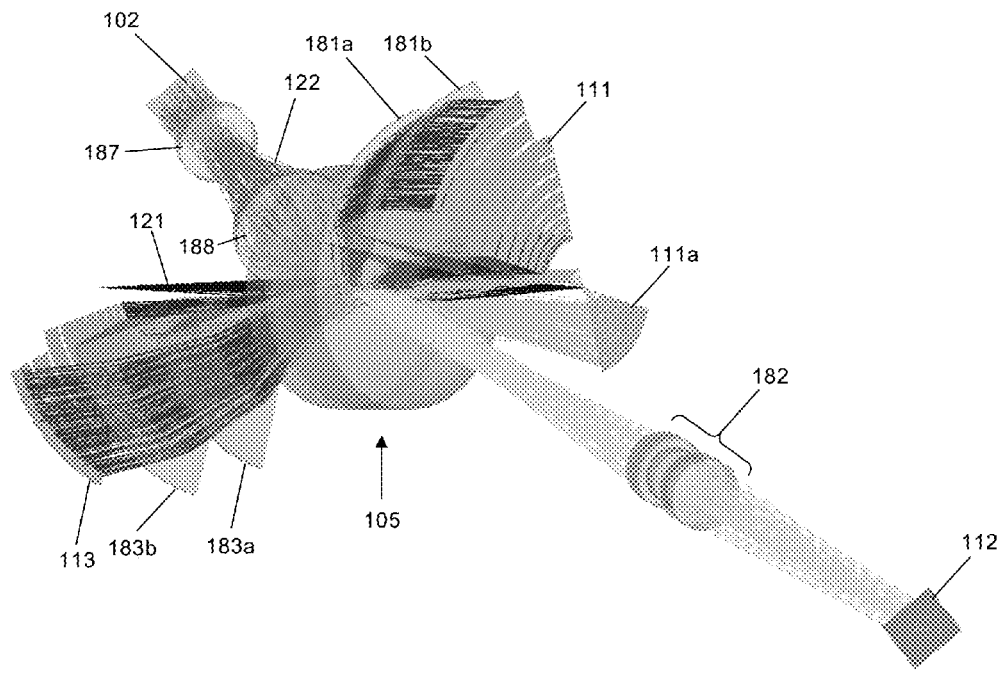
FIG. 5 is a ray diagram of a further example of an instrument with a back-scattered light detector, a forward-scattered light detector, and an imaging detector with light field illumination.

FIG. 5 shows a further example of scattering instrument, which is similar to that of FIG. 4. In FIG. 5 the schematic illustration imaging lens 182 have been replaced with a group of lens elements that together comprise the imaging lens 182, and the second detector 112 has been repositioned based on the design of the imaging lens 182. The second light source 102 and associated optics are the same as described with respect to FIG. 4, as is the sample cell 105, first detector 111 and associated collection lenses 181a, 181b, and the third detector 113 and associated collection lenses 183a, 183b.

FIG. 5 includes a further detector 111a, for detecting light scattered from the sample 150 at low forward scattering angles (i.e. at a range of scattering angles that includes angles smaller than the range of scattering angles received by the first detector 111). Light scattered by the interaction of the first light beam 121 with the sample 150 is focussed by the second sample cell wall 162 at the further detector 111a. The further detector 111a may be configured to detect light scattered at angles of less than 1° to angles of at least 10°, for instance, from 0.1° to 15°.

Figure 6:
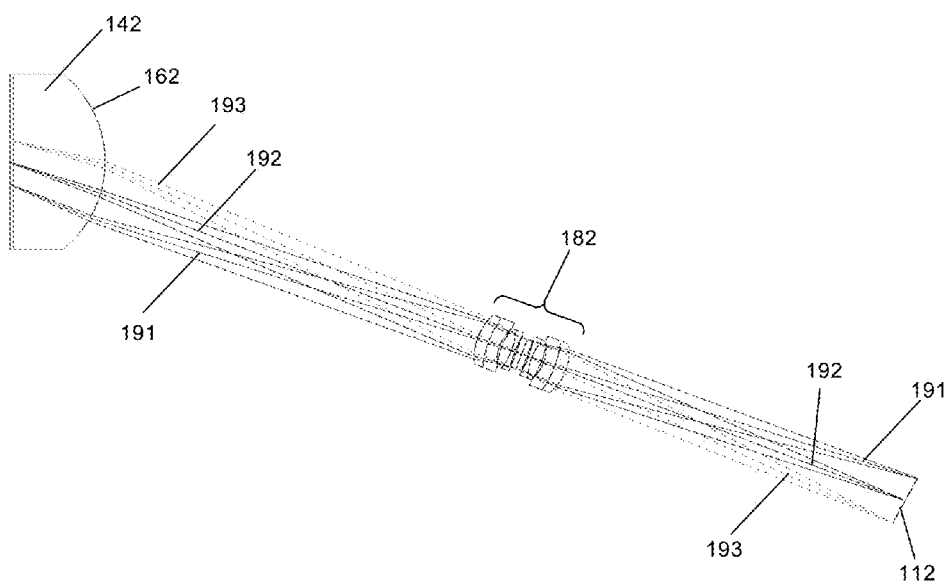
FIG. 6 is a ray diagram of an optical arrangement for an imaging detector and associated focussing optics for a lensed sample cell including the second wall of the sample cell.
Figure 7:
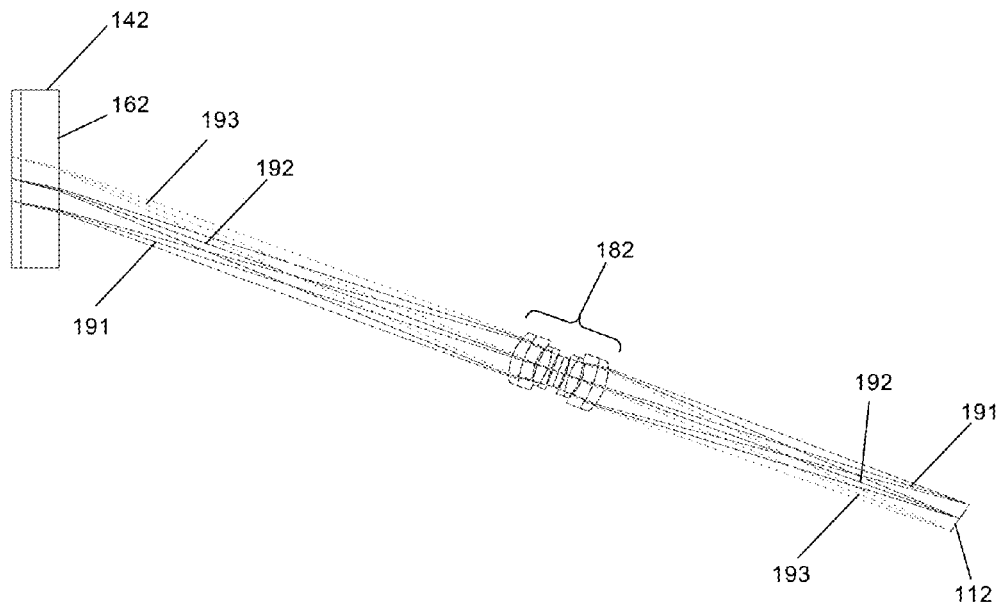
FIG. 7 is a ray diagram of a an optical arrangement for an imaging detector and associated focussing optics for a flat sample cell, including the second wall of the sample cell.

FIG. 6 illustrates the optical arrangement of the second sample cell wall 142, imaging lens 182 and second detector 112, showing the path of a first, second and third bundle of rays 191, 192, 193, corresponding with lower, mid and upper locations within the imaging region of the sample cell 105. This can be compared with a similar illustration for a sample cell with flat walls, shown in FIG. 7.

A further benefit of the second sample cell wall 142 comprising a lens is that the image height, or numerical aperture of the imaging arrangement is increased. In example embodiments, and increase in numerical aperture of around 1.6 is possible.

Figure 8:
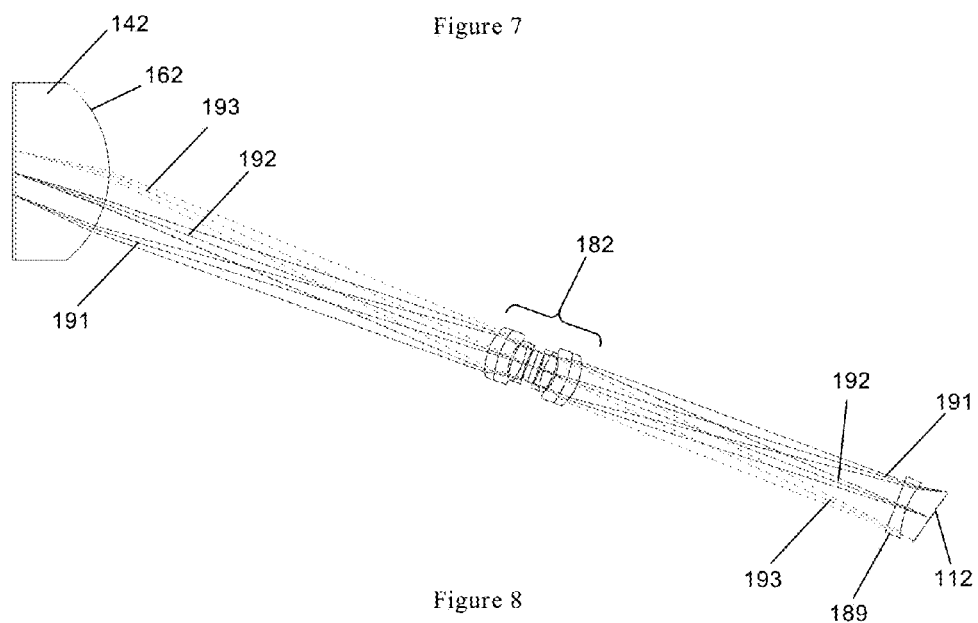
FIG. 8 is a ray diagram of an optical arrangement for an imaging detector and associated focussing optics for a lensed sample cell including the second wall of the sample cell, in which the focussing optics comprise a field correction lens between the imaging detector and the main focussing optical group.

FIG. 8 illustrates an example imaging optical arrangement which is similar to that of FIG. 6, in which a field flattener lens 189 has been included to at least partially compensate for the inclined imaging axis with respect to the sample cell 105. This may improve image quality at the second detector 112.

In an alternative arrangement (not shown), the sample cell 105 may be in a different position than shown in FIGS. 4 and 5. Instead of aligning the first (scattering) light beam axis with the optical axis of the sample cell 105 (the sample cell optical axis being defined by the optical axes of the first and second sample cell walls 141, 142), the sample cell optical axis may be aligned (or coincident with) the imaging axis of the second (imaging) detector 112. This may improve the quality with which the sample is imaged by the second detector 112. The scattering arrangement may be substantially unaffected by this change, due to the reduced refraction at the sample cell/air interfaces resulting from the convex cell surfaces 161, 162.

A number of other variations are possible within the scope of the invention, which is defined by the appended claims.

The invention claimed is:

1. A particle characterisation apparatus comprising: a first light source; a second light source, a sample cell; a first detector, a second detector, and a processor; wherein:
   the first light source is operable to illuminate a first region of a sample comprising dispersed particles within the sample cell with a first light beam along a first light beam axis so as to produce scattered light by interactions of the first light beam with the sample;
   the first detector is configured to detect the scattered light;
   the second light source is operable to illuminate a second region of the sample with a second light beam along a second light beam axis;
   the second detector is an imaging detector, configured to image the particles along an imaging axis using the second light beam;
   the first light beam axis is at an angle of at least 5 degrees to the second light beam axis; and
   the processor is configured to correlate or cross-reference output from the first detector with output from the second detector to perform a light diffraction measurement to derive a particle size.

2. The particle characterisation apparatus of claim 1, wherein the sample cell comprises a first wall and a second wall, and the first light beam passes through the first wall, then through the sample, then through the second wall, wherein the first and second wall of the sample cell each comprise a convex external surface through which the first light beam axis and the second light beam axis passes.

3. The particle characterisation apparatus of claim 2, wherein the first and second wall each comprise a plano-convex lens defined by the respective convex external surface, the optical axes of the first and second wall defining a sample cell optical axis.

4. The particle characterisation apparatus of claim 3, wherein the second light beam axis is at an angle of at least 10° to the sample cell optical axis.

5. The particle characterisation apparatus of claim 1, wherein the first light source, sample cell and first detector define a scattering plane, and the second light source and second detector are disposed offset from the scattering plane, occupying a different azimuthal orientation about the first light beam axis.

6. The particle characterisation apparatus of claim 1, comprising a collecting lens between the sample cell and the first detector, wherein the collecting lens comprises an aspheric surface.

7. The particle characterisation apparatus of claim 6, wherein the collecting lens comprises an optical axis that is coincident with the first light beam axis.

8. The particle characterisation apparatus of claim 1, comprising a processor, wherein the processor is configured to correct a size of an imaged particle based on a location of the particle image at the second detector.

9. The particle characterisation apparatus of claim 1, comprising a condenser lens between the second light source and the sample cell and a collector lens between the condenser lens and the second light source, wherein the second light source, collector lens and condenser lens are arranged to provide Köhler illumination of a region within the sample cell.

10. The particle characterisation apparatus of claim 1, wherein the second detector is arranged on a path of the second light beam, so as to perform light field imaging of particles within the sample cell.

11. The particle characterisation apparatus of any claim 1, wherein the second detector is arranged off the path of the second light beam, so as to perform dark field imaging of particles within the sample cell.

12. The particle characterisation apparatus of claim 10, comprising a third light source arranged to provide a third light beam that is not directly received by the second detector, so that the apparatus is configured to perform dark field imaging when the sample is illuminated by the third light source and not by the second light source.

13. The particle characterisation apparatus of claim 1, wherein the first region is at least partly coincident with the second region.

14. The particle characterisation apparatus of claim 1, wherein the second detector is configured to image the sample along an imaging axis, and the imaging axis is at an angle of at least 5 degrees to the first light beam axis.

* * * * *